United States Patent
Purandare et al.

(10) Patent No.: US 11,515,005 B2
(45) Date of Patent: Nov. 29, 2022

(54) INTERACTIVE-AWARE CLUSTERING OF STABLE STATES

(71) Applicant: International Business Machines Corporation, Armonk, NY (US)

(72) Inventors: Mitra Purandare, Zurich (CH); Matteo Manica, Zurich (CH); Raphael Polig, Langnau am Albis (CH); Maria Rodriguez Martinez, Thalwil (CH)

(73) Assignee: International Business Machines Corporation, Armonk, NY (US)

( * ) Notice: Subject to any disclaimer, the term of this patent is extended or adjusted under 35 U.S.C. 154(b) by 588 days.

(21) Appl. No.: 16/284,470

(22) Filed: Feb. 25, 2019

(65) Prior Publication Data

US 2020/0273539 A1    Aug. 27, 2020

(51) Int. Cl.
| | |
|---|---|
| *G01N 33/48* | (2006.01) |
| *G01N 33/50* | (2006.01) |
| *G16B 20/50* | (2019.01) |
| *G06K 9/62* | (2022.01) |
| *G06F 17/16* | (2006.01) |
| *G16B 5/10* | (2019.01) |
| *G06F 17/13* | (2006.01) |

(52) U.S. Cl.
CPC ............ *G16B 20/50* (2019.02); *G06F 17/13* (2013.01); *G06F 17/16* (2013.01); *G06K 9/6223* (2013.01); *G06K 9/6248* (2013.01); *G16B 5/10* (2019.02)

(58) Field of Classification Search
CPC .......... G16B 20/50; G16B 5/10; G16B 20/00; G16B 40/30; G06K 9/6223; G06K 9/6248; G06K 9/6224; G06K 9/6219; G06F 17/16; G06F 17/13
See application file for complete search history.

(56) References Cited

U.S. PATENT DOCUMENTS

| | | | |
|---|---|---|---|
| 9,542,641 B2 | 1/2017 | Abdi et al. | |
| 2011/0191087 A1 | 8/2011 | Lehrach et al. | |
| 2012/0191357 A1* | 7/2012 | Qiu | G16B 40/30 702/19 |
| 2014/0214336 A1* | 7/2014 | Martin | G16H 50/30 702/19 |
| 2016/0103971 A1 | 4/2016 | Hillis et al. | |

FOREIGN PATENT DOCUMENTS

WO    2017/160842 A1    9/2017

OTHER PUBLICATIONS

Vaske et al. Inference of patient-specific pathway activities from multi-dimensional cancer genomics data using PARADIGM. Bioinformatics, vol. 26, pp. i237-i245. (Year: 2010).*

(Continued)

*Primary Examiner* — Russell S Negin
(74) *Attorney, Agent, or Firm* — Scully, Scott, Murphy & Presser, P.C.; Daniel P. Morris

(57) ABSTRACT

Analysis of genetic disease progression may be provided. Data about a set of molecular status may be received. A dynamic prediction model of molecular interactions may be provided over time. The molecular statuses of the set over time may be determined using the dynamic prediction model. The determined molecular statuses may be clustered by applying an interaction-aware metric for the analysis of the genetic disease progression.

20 Claims, 5 Drawing Sheets

(56) References Cited

OTHER PUBLICATIONS

Bharath et al. Molecular modeling of the chromatosome particle. Nucleic Acids Research, vol. 31, pp. 4264-4274. (Year: 2003).*

Fumia, H.F., et al., "Boolean Network Model for Cancer Pathways: Predicting Carcinogenesis and Targeted Therapy Outcomes", PLoS One, Jul. 2013, pp. 1-11, vol. 8, Issue 7.

Garg, A., et al., "Synchronous versus asynchronous modeling of gene regulatory networks", Bioinformatics, Received on Feb. 1, 2008, revised on Jun. 10, 2008, accepted on Jul. 1, 2008, Advance Access publication Jul. 9, 2008, pp. 1917-1925, vol. 24, No. 17.

Glass, L., et al., "The Logical Analysis of Continuous Non-Linear Biochemical Control Networks", J. Theor. Biol. 1973, received May 8, 1972, revised Aug. 22, 1972, pp. 103-129, vol. 39.

Greico, L., et al., "Integrative Modelling of the Influence of MAPK Network on Cancer Cell Fate Decision", PLoS Computational Biology, Oct. 2013, pp. 1-15, vol. 9, Issue 10.

Hanahan, D., et al., "Hallmarks of Cancer: The Next Generation", Cell 144, Mar. 4, 2011, pp. 646-674.

Hu, Y., et al., "Integrated network model provides new insights into castration-resistant prostate cancer", Scientific Reports, received Apr. 2, 2015, accepted Oct. 28, 2015, published Nov. 25, 2015, pp. 1-12, 5:17280.

Kauffman, S, et al., "Homeostasis and Differentiation in Random Genetic Control Networks", Nature, Oct. 11, 1969, pp. 177-178, vol. 224.

Koch, L., "Complex Disease: A Global View of Regulatory Networks", Nature Reviews Genetics, Mar. 21, 2016, 1 page.

Lu, J., et al., "Network modelling reveals the mechanism underlying colitis-associated colon cancer and identifies novel combinatorial anti-cancer targets", Scientific Reports, received Jan. 15, 2015, accepted Sep. 7, 2015, published Oct. 8, 2015, pp. 1-15, 5:14739.

Rodriguez, A., et al., "A Boolean network model of the FA/BRCA pathway", Bioinformatics, Received on Sep. 1, 2011, revised on Jan. 13, 2012, accepted on Jan. 16, 2012, Advance Access publication Jan. 20, 2012, pp. 858-866, vol. 28, No. 6.

Thomas, R., "Regulatory Networks Seen as Asynchronous Automata: A logical Description", Journal of Theoretical Biology (1991), received and Accepted Apr. 3, 1991, pp. 1-23, vol. 153.

Zhang, R., et al., "Network model of survival signaling in large granular lymphocyte leukemia", Proceedings of the National Academy of Sciences (PNAS), Oct. 21, 2008, pp. 16308-16313, vol. 105, No. 42.

* cited by examiner

| gene name | regulatory function |
|---|---|
| ICL | ICL and not DSB |
| FANCM | ICL and not CHKREC |
| DSB | (DSB or FAN1 or XPF) and not (NHEJ or HRR) |
| CHKREC | ((PCNATLS or NHEJ or HRR) and not DSB) or ((not ADD) and (not ICL) and (not DSB) and not CHKREC) |

INTERACTIVE-AWARE CLUSTERING OF STABLE STATES

BACKGROUND

The present disclosure relates generally to understanding disease progression, and more specifically, to a computer-implemented method for an efficient analysis of genetic disease progression. The present disclosure relates further to a related disease analysis system for an efficient analysis of genetic disease progression, and a computer program product.

Cancer is a complex, multi-factorial disease caused by an accumulation of genetic mutations that target important molecular pathways for the cell functioning. Dysregulation of these pathways endows the cell with new capabilities that enable tumor growth and metastatic dissemination, such as proliferative signaling, evading growth suppressors, resisting cell death and immune destruction, reprogramming of energy metabolism, enabling replicative immortality, inducing angiogenesis, and activating invasion and metastasis.

For a patient suspected to suffer from cancer, generally, a tumor biopsy is performed and certain measurements like gene translation (mRNAs), transcription (proteins), phosphorylation, methylation, copy number alterations etc. are performed. This data is ultimately used for a diagnosis and deciding the next course of therapy. To enable systematic diagnosis and therapy, it is important to know how the disease progresses. Given the patient state, dynamic models of the molecular pathways involved in the disease are necessary to simulate disease progression.

Genes are the basic building blocks that control all cellular functions in an organism. Genes do not work in isolation, but exert their function in complex and tightly regulated gene regulatory networks (GRNs). At the very basis, understanding health and disease amounts to unravelling the normal and dysregulated behavior of GRNs. With the development of advanced high-throughput technologies, the availability of experimental data about the molecular interactions within the cell has reached unprecedented volumes and accuracy. This has led to amassing tremendous wealth of molecular information, e.g., gene-gene interactions and protein-protein interactions.

SUMMARY

According to one aspect of the present invention, a computer-implemented method for an efficient analysis of genetic disease progression may be provided. The method may comprise receiving data about a set of molecular statuses and providing a dynamic prediction model of molecular interactions over time. The method may comprise further determining the molecular statuses of the set over time using the dynamic prediction model, and clustering the determined molecular statuses by applying an interaction-aware metric for the analysis of the genetic disease progression.

According to another aspect of the present invention, a disease analysis system for an efficient analysis of genetic disease progression may be provided. The system may comprise a receiving unit adapted for receiving data about a set of molecular statuses, and a prediction module adapted for a dynamic prediction model of molecular interactions over time.

Additionally, the system may comprise a determination unit adapted for determining the molecular statuses of the set over time using the dynamic prediction model, and a clustering module adapted for clustering the determined molecular statuses by applying an interaction-aware metric to analyze genetic disease progression.

Furthermore, embodiments may take the form of a related computer program product, accessible from a computer-usable or computer-readable medium providing program code for use, by, or in connection, with a computer or any instruction execution system. For the purpose of this description, a computer-usable or computer-readable medium may be any apparatus that may contain means for storing, communicating, propagating or transporting the program for use, by, or in connection, with the instruction execution system, apparatus, or device.

BRIEF DESCRIPTION OF THE DRAWINGS

It should be noted that embodiments of the invention are described with reference to different subject-matters. In particular, some embodiments are described with reference to method type claims, whereas other embodiments are described with reference to apparatus type claims. However, a person skilled in the art will gather from the above and the following description that, unless otherwise notified, in addition to any combination of features belonging to one type of subject-matter, also any combination between features relating to different subject-matters, in particular, between features of the method type claims, and features of the apparatus type claims, is considered as to be disclosed within this document.

The aspects defined above, and further aspects of the present invention, are apparent from the examples of embodiments to be described hereinafter and are explained with reference to the examples of embodiments, but to which the invention is not limited.

Figure 1:
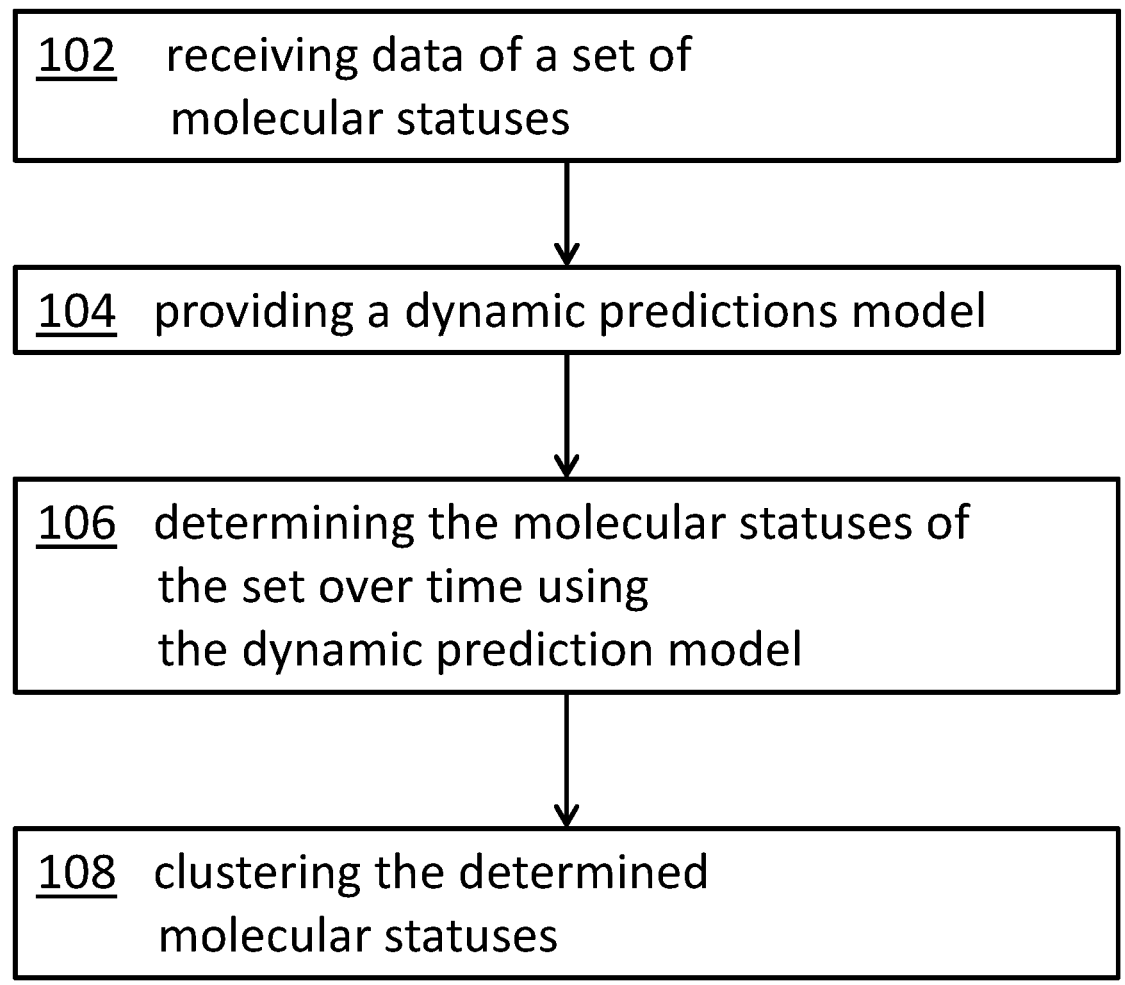

Preferred embodiments of the invention will be described, by way of example only, and with reference to the following drawings:

FIG. 1 shows a block diagram of an embodiment of the inventive computer-implemented method for an efficient analysis of genetic disease progression.

Figures 2A, 2B:
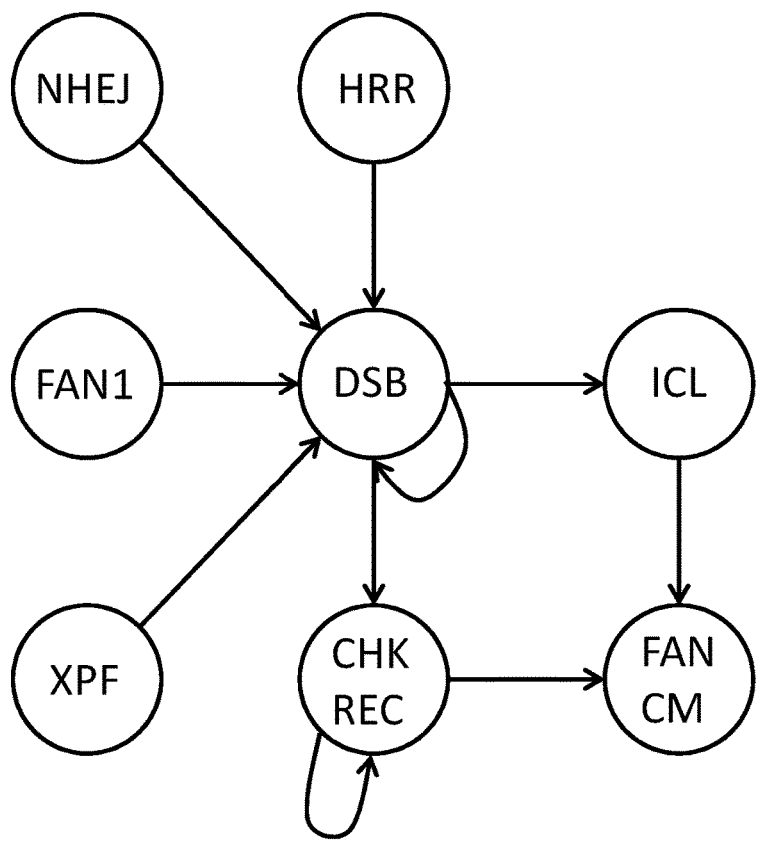

FIGS. 2A-2B show a block diagram of an embodiment of a gene regulatory network (a) together with a Boolean model of a particular FA-BRCA pathway.

Figure 3:
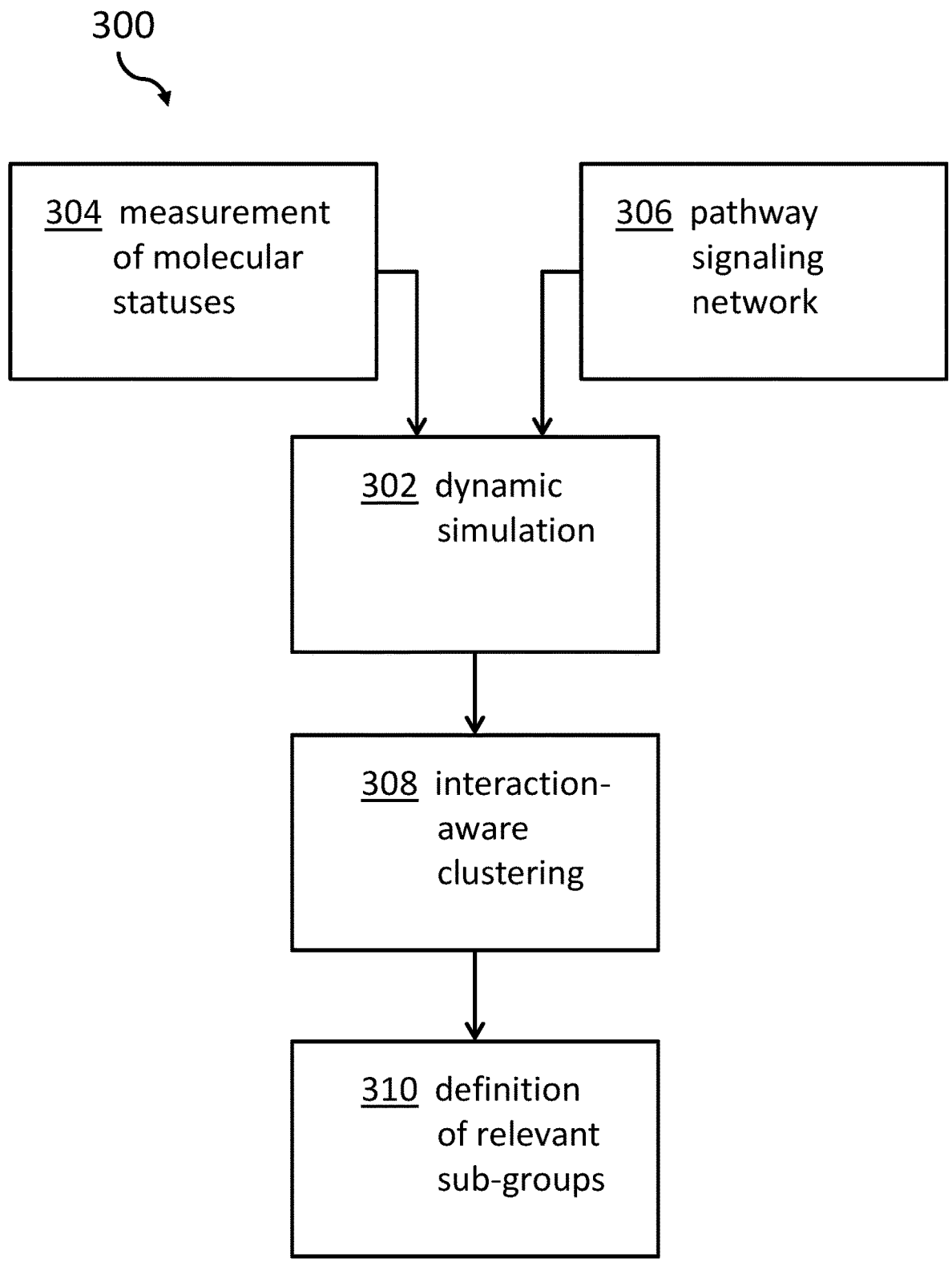

FIG. 3 shows a block diagram of an embodiment of the proposed method in a more realistic and implementable form.

Figure 4:
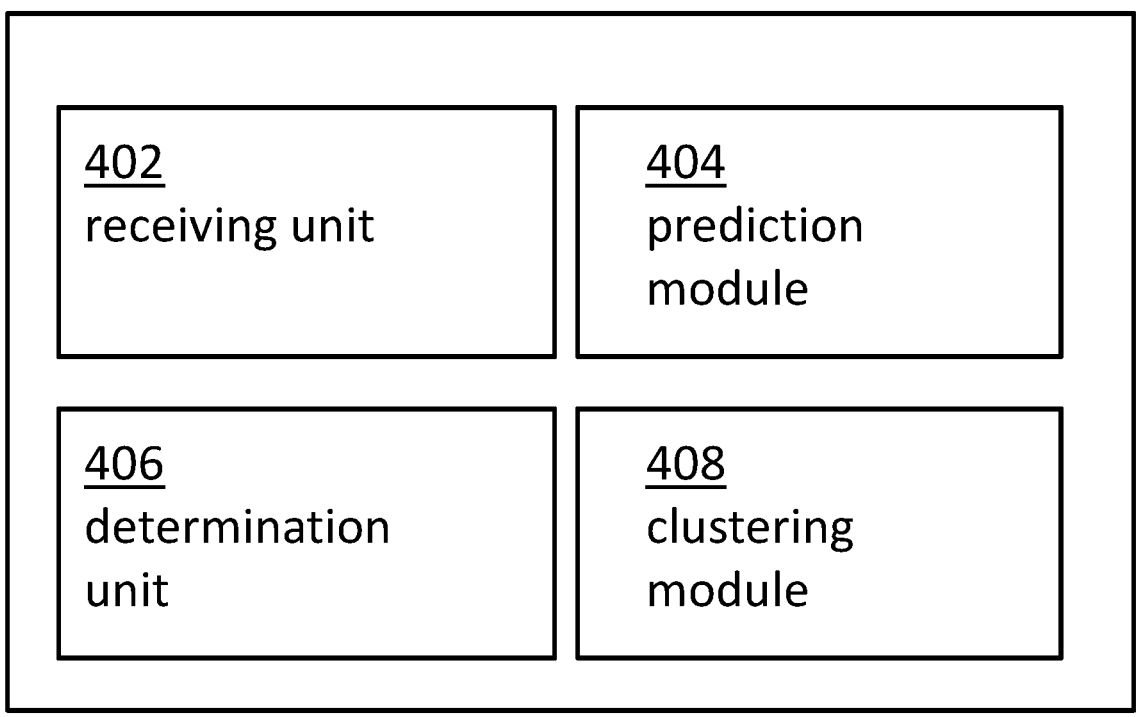

FIG. 4 shows an embodiment of the disease analysis system.

Figure 5:
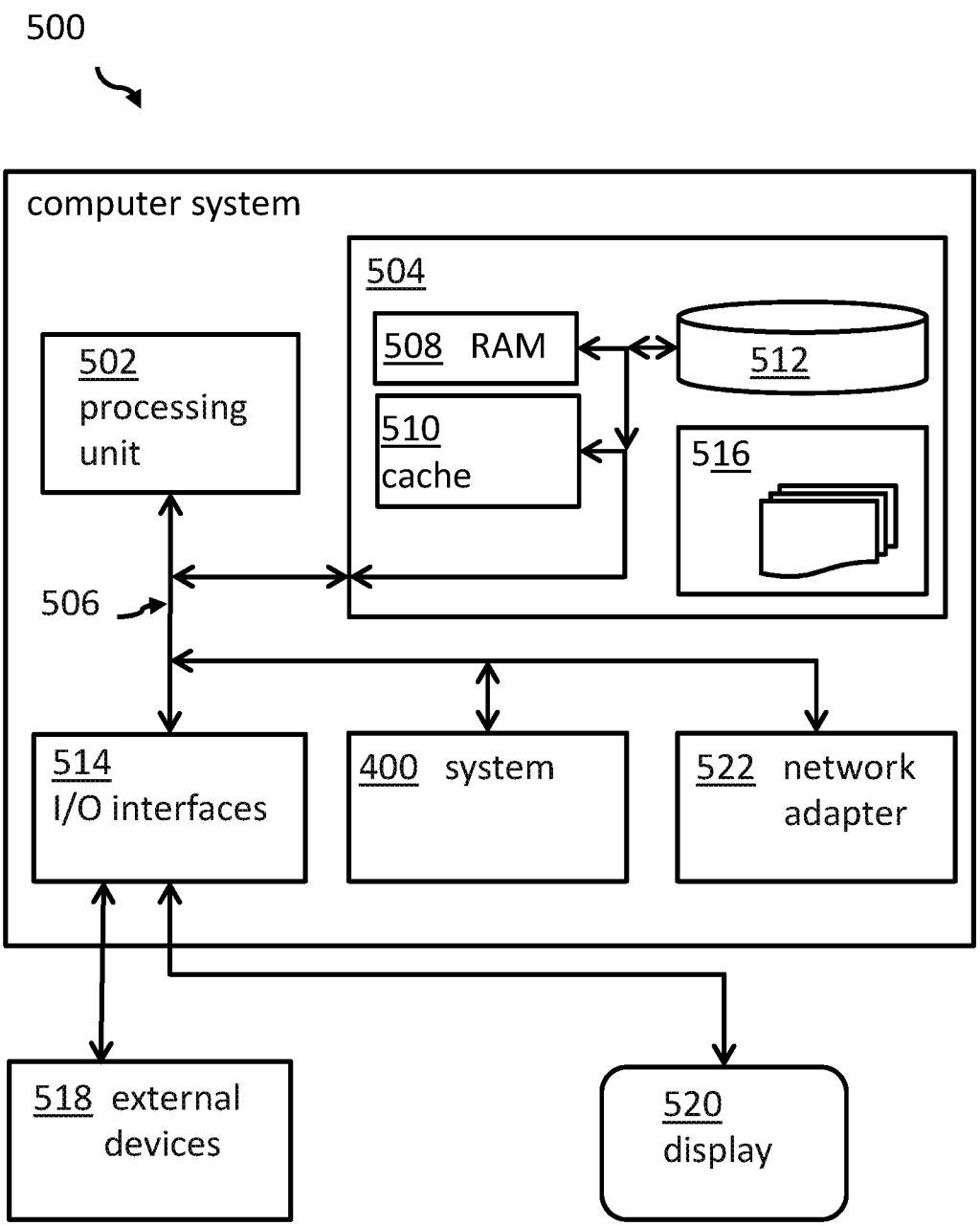

FIG. 5 shows an embodiment of a computing system comprising the disease analysis system according to FIG. 4.

DETAILED DESCRIPTION

In the context of this description, the following conventions, terms and/or expressions may be used:

The term 'genetic disease progression' may denote a measurement metric of the speed of spreading of disease relevant factors in a biological environment, e.g., a living body, or a cell line. This may relate to an individual patient and an average of a patient group. The same may apply to a cell line of a group of different but similar cell lines. Simply speaking, the genetic disease progression may measure the speed in which a disease spreads on the constraints of gene regulatory networks.

The term 'molecular status' may denote a measured values of statuses (or states) of a gene, a set of genes or other disease relevant concentrations or parameters indicative of a disease status.

The term 'dynamic prediction model' may denote an artificial development model of future developments of molecular statuses depending on predefined (known) constraints and/or dependencies. This dynamic prediction model has time as the most important variable. Thus, the dynamic prediction model may allow statements of future statuses of model parameters over time.

The term 'molecular interaction' may denote an influence of a concentration of a gene and/or biological material on another gene. Typically, molecular interactions are multidimensional, i.e., there is not only one enforcing or damping force or factor but a plurality of those factors.

The term 'clustering' may denote the activity of grouping a set of objects—in particular measurement values—in such a way that objects in the same group—i.e., the same cluster—are more similar (in some sense) to each other than to those in another group—i.e., another cluster. Clustering is a known technique for statistical data analysis. There is not one single cluster analysis algorithm but the general task to be solved. It may be achieved by a variety of different algorithms that differ significantly in their understanding of what constitutes a cluster and how to efficiently find it. Popular notions of clusters may include groups with small distances between cluster members, dense areas in the data space, intervals or particular statistical distributions. Some examples are given later.

The term 'interaction-aware metric' may denote a framework of determining distances considering the network topology of the interacting genes. From another perspective one may also say to also take into account a set of constraints having a significant influence on the genetic disease progression. Without the interaction-aware metric there would basically be not any influencing factors. However, taking into account the interaction between different enhancing and damping (i.e., activating and inhibiting) factors, a very realistic simulation and thus a subsequence clustering of predicted data pair (or triplets or larger groups) may be possible.

The term 'Boolean model' may denote a digital interaction model between different gene statuses. In the Boolean model there are only the two options "has influence" or "not has influence" (alternatively: "is positively influencing" or "is negatively influencing"). Thus, the Boolean model may represent the simplest form of interaction awareness. Other, more advanced interaction models may be based on a linear dependency, quadratic dependency or higher order mathematical dependencies.

The term 'Laplacian matrix' may denote in the field of graph theory, a matrix representation of a graph. The Laplacian matrix can be used to find many useful properties of a graph. Sometimes the Laplacian matrix may also be denoted admittance matrix, Kirchhoff matrix or discrete Laplacian. Together with Kirchhoff s theorem, it may be used to calculate the number of spanning trees for a given graph. Special forms of the Laplacian are known as 'deformed Laplacian matrix', 'symmetric Laplacian matrix' or 'random walk Laplacian matrix'.

The term 'Vicus matrix' may denote an alternative to the Laplacian matrix; in particular, the Vicus matrix may capture the local neighborhood structure of a network and thus may be more effective at modeling biological interactions. The Vicus matrix and transformation may take advantage of the local structure of the network while preserving algebraic properties of the Laplacian.

The term 'k-means' may denote a method of vector quantization, originally from signal processing, that is popular for cluster analysis in data mining k-means clustering aims to partition n observations into k clusters in which each observation belongs to the cluster with the nearest mean, serving as a prototype of the cluster. This results in a partitioning of the data space into Voronoi cells.

The term 'DB SCAN' (Density-Based Spatial Clustering of Applications with Noise) may denote a special clustering algorithm proposed in 1996. It is a density-based clustering algorithm: given a set of points in some space, it groups together points that are closely packed together (points with many nearby neighbors), marking as outliers points that lie alone in low-density regions (whose nearest neighbors are too far away).

The term 'hierarchical clustering' (also called hierarchical cluster analysis or HCA) may denote a method of cluster analysis which seeks to build a hierarchy of clusters. Strategies for hierarchical clustering may generally fall into two types: (i) agglomerative: This is a "bottom-up" approach: each observation starts in its own cluster, and pairs of clusters are merged as one moves up the hierarchy; (ii) divisive: This is a "top-down" approach: all observations start in one cluster, and splits are performed recursively as one moves down the hierarchy. In general, the merges and splits are determined in a greedy manner. The results of hierarchical clustering may usually be presented in a dendogram.

The proposed computer-implemented method for an efficient analysis of genetic disease progression may offer multiple advantages and technical effects:

The results of the proposed concept may be applied to a wide variety of clinical and/or industrial application areas. These may comprise finding patience sub-groups to define personalized therapies. This may reduce the amount of drugs to be consumed by a patient significantly which may also reduce significantly undesired side effects.

On the other side, product tests may be performed in silico (in vitro) for a testing of new drugs and drug discovery. This may reduce the requirement for experiments on living organisms.

Furthermore, it may elegantly become possible to determine disease sub-types that give rise to different prognosis for the same base-disease.

In the following, additional embodiments of the method—also applicable to the related model—will be described:

According to one embodiment of the method, the dynamic prediction model may be selected out of the group comprising a Boolean model, a set of ordinary differential equations, a set of stochastic differential equations, a set of partial differential equations. Basically, every prediction model may be used. This gives the proposed concept a high flexibility in the simulation algorithms.

According to one embodiment of the method, the data of the set of molecular statuses may be represented by measurement values of a patient, a cell line or drug perturbations. Hence, the data may represent real world data capturing a real status of a living body (in vivo) or the data may originate from a cell line (in vitro) or a distribution over time of drugs in a living body or in a cell line. Thus, the proposed concept may be adapted to many different types of measured data values.

According to one embodiment of the method, the dynamic prediction model and related parameters may be downloadable from a database—in particular, remote or local database. The download may be performed over a suitable network and the storage—i.e., remote database (also a local database may be used)—may be part of a cloud data center. Thus, modern storage and data transmission technologies may be used in the context of the here proposed concept. Additionally, graphical tools may be used to display results of the clustering, i.e., the analysis over time.

According to one embodiment of the method, the interaction-aware metric may be at least in parts based on a Laplacian matrix, a deformed Laplacian matrix, a symmetric Laplacian matrix, a random walk Laplacian matrix and/or a Vicus matrix. Thus, the dependencies—i.e., the interactions between different components of the molecular statuses—may be models fine-grained and according to the latest insights in respective mutual and/or reciprocal bidirectional or multidimensional influences.

According to an embodiment of the method, the analysis of the genetic disease progression may comprise determining an optimized personalized therapy, i.e., an optimized mix of drugs to cure a severe disease. Because the influence of the drug(s) may be predicted in a model very close to the reality of a patient represented by the respective molecular statuses, as little as possible drugs may be administered in order to cure the patient without having a too negative influence on the organism (e.g., in chemotherapy based cancer treatments).

According to an embodiment, the method may also comprise determining a disease sub-type based on the clustering. Thus, different sub-types of a disease may lead to a different clustering of the simulation. One example may be a simulation disease development of leukemia. Here, some types of the disease are curable with a good chance of success; in other cases it is not possible to cure it at all. Such a prediction may be very valuable for a patient.

According to an embodiments of the method, the clustering may be based on—i.e., directly may use—at least one algorithm selected out of the group k-means, DBSCAN, and hierarchical clustering. However, also other suitable algorithms may be implemented together with the here proposed concept. Thus, the proposed concept may choose from a larger variety of well researched algorithms.

According to one embodiment of the method, as distance measure during the clustering a Manhattan distance or an Euclidean distance is determined. Such distance model may advantageously be combined with the above-mentioned clustering models. Hence, a researcher using the proposed concept may make use of a complete toolset of simulation models and sub-algorithms.

According to another embodiment of the method, the distance determination may also be a function of the interaction-aware metric. Thus, a convolution of the different influence factors—e.g., distance determination as well as interaction-aware metric—may be used in order to get an optimized simulation, i.e., analysis model.

In the following, a detailed description of the figures will be given. All instructions in the figures are schematic. Firstly, a block diagram of an embodiment of the inventive computer-implemented method for a computer-implemented method for an efficient analysis of genetic disease progression is given. Afterwards, further embodiments, as well as embodiments of the disease analysis system for an efficient analysis of genetic disease progression, will be described.

FIG. 1 shows a block diagram of an embodiment of the computer-implemented method 100 for an efficient analysis of genetic disease progression. The method 100 comprises receiving, 102, data about a set of molecular statuses, in particular from a single patient, a class of patients, proteomics, transcriptomics, genomics or similar sources.

The method 100 comprises additionally providing, 104, a dynamic prediction model of molecular interactions over time. This involves the molecules for which the data about the molecular statuses have been received.

Furthermore, the method 100 comprises determining, 106—in particular simulating—the molecular statuses of the set over time using the dynamic prediction model, and clustering, 108, the determined molecular statuses by applying an interaction-aware metric for the analysis of the genetic disease progression.

To be more specific, a network graph G=(V, E) may be considered, wherein V is a set of vertices and D the set of directed or undirected edges. It may be considered an undirected version of a directed graph G⁻ obtained by dropping the edges directions in the graph. If D is the degree matrix and A the adjacency matrix for G⁻, then the Laplacian matrix used here as an exemplary transformation matrix—may be applied in the context of the proposed concept in the following way:

As a reminder, in the mathematical field of graph theory, the Laplacian matrix is a matrix representation of a graph. If n is the number of vertices, the Laplacian is a square matrix with n columns and n rows. Determining the Laplacian using D and A is performed by $$L=D-A$$

Wherein $L_{i,j}$=deg $(v_i)$, if i=j, and deg $(v_i)$ is the degree of the vortex i. $L_{i,j}$=−1 if i≠j and $v_i$ is adjacent to $v_j$. $L_{i,j}$=0, otherwise.

For undirected graphs, L is a semi-definite positive, symmetric matrix. The Laplacian represents a discrete diffusion process on the graph. It may be used to compute distances with a re-weighted metric. Given the status $S_i$ on the vertices of the graph, one can determine a distance from $S_j$ using the following formula:

$$(S_i-S_j)^T L(S_i-S_j)$$

This short excurse may be considered as a base of a model for the interaction-aware metric.

FIGS. 2A-2B show a block diagram of an embodiment of a gene regulatory network (FIG. 2A) together with a Boolean model of a particular FA-BRCA pathway. The figure shows a partial directed network from the FA-BRCA (Fanconi Anemia/Breast Cancer) pathway. Each circle node represents a gene. An edge in a gene regulatory network indicates the direction of the interaction between genes and the type of interaction, namely activating or inhibiting. In FIG. 2A, the gene ICL is suppressed but the gene DSB (DSB-•ICL), whereas the gene XPF activates the gene DBS (XPF→DSB).

As already mentioned, the Boolean model provides a qualitative description of a gene regulatory network, wherein chemical species concentrations are activities using infinite sets of discrete values. In its simplest form, a gene can be ON ('1') or off ('0'), and its interaction with others can be defined as the Boolean function of its record relating genes, i.e., its parent nodes in the gene regulatory network. In this context, time is represented by discrete steps, and depending on the order in which the Boolean functions are evaluated and assigned to the respective genes. Various updates schemes are possible.

In a synchronous scheme, all genes are simultaneously evaluated and, resulting in a fully deterministic computationally traceable system, although often biologically unrealistic. Conversely, the synchronous scheme randomly chooses a gene and updates it to its next value. The synchronous scheme provides a stochastic, and hence more realistic, description of a gene regulatory network, although the price of the computational complexity and the runtime of the model increases greatly. In addition, as the model is stochastic, it has to run multiple times in order to resolve the means dynamic behavior.

FIG. 2B illustrates how regulatory function of some genes of FIG. 2A can be expressed as the Boolean formula. For example, the second row indicates that the genes ICL and CHKREC are the regulators of the gene FANCM. The corresponding regulatory function as ICL and not CHKREC, i.e., the gene FANCM is active only when ICL is active and CHKREC is inactive.

Although a Boolean model cannot provide the level of detailed information that an experimentally well-characterized differential equation system (SDE, ODP, PDE—compare below) may provide, it may produce a qualitative description of the most salient features of a dynamical system, a Boolean model may provide important insights into its dynamics. For instance, Boolean models may be very useful to identify steady statuses, cyclic statuses are attractors.

Other interaction-aware models than the Boolean model may also be used as part of the here described concept. However, in the following, the Boolean model is explained in that little bit more detailed fashion. A lot of research has been done to develop their TCGO (The Cancer Genome Atlas) with many samples from more than 10,000 patients and across more than 30 tumor types. The following table 1 depicts exemplary the gene transcription profile for a number of patients before and after decentralization:

TABLE 1

| #patient | AKT1 | AKT2 | AKT3 | AKT4 | AKT4 |
|---|---|---|---|---|---|
| 1 | 9.46 | 8.74 | 7.76 | 6.38 | 7.87 |
| 2 | 9.31 | 8.62 | 8.12 | 6.45 | 8.06 |
| 3 | 9.52 | 9.10 | 8.04 | 8.61 | 8.10 |
| 4 | 9.41 | 8.53 | 8.02 | 6.06 | 8.06 |
| 5 | 9.56 | 8.62 | 8.05 | 5.83 | 8.07 |

The first column comprises a patient identifier. The remaining columns have the gene transcription data for each gene, PTEN, PSA, ACK1, etc. Each row gives the gene transcription information for each patient.

The related table 2 shows the discretized gene expression values characteristic to each patient and represent his/her disease state in the Boolean model.

TABLE 2

| #patient | AKT1 | AKT2 | AKT3 | AKT4 | AKT4 |
|---|---|---|---|---|---|
| 1 | — | — | — | — | — |
| 2 | — | — | ON | — | ON |
| 3 | ON | ON | ON | ON | ON |
| 4 | — | OFF | — | — | ON |
| 5 | ON | — | ON | OFF | OFF |

According to the discretized disease state of a patient, the initial values of gene nodes in the Boolean model are initialized. Then asynchronous simulations are performed for a desired number of times steps (t), each time evaluating and updating the node values in a random generated order. Since these are stochastic simulations, the simulations are repeated r times. This gives rise to r values for each node at each time step t.

Then the number of times a node was "1"/"0" at specific time points in all the repetitions is determined. Using this, the frequency of activation (node value=1) for each node at each time step is determined.

It may be noted to repeat the simulations many times (r>1000). If a simulation is repeated very few times, the activation frequencies do not converge, as can be shown. The frequency curve for apoptosis for 10 or 100 repetitions is not smooth. A similar unstable curve can be observed for BID as well. As the number of repetitions is increased, the related curves start to look smoother.

For each repetition, a timestamp is considered when all the frequencies are stabilized. This matches with a stable/steady-state for that repetition. The values of nodes giving rise to a steady-state are then collected. This gives rise to r steady states which need to be clustered to enable better understanding of the disease. It may again be noted that this exemplary model relates to a usage of the Boolean model.

FIG. 3 shows a block diagram of an embodiment 300 of the proposed method in a more realistic and implementable form. The dynamic simulation 302 may receive two sets of input data: from the top of the left side, data from molecular measurements 304 from, e.g., patience, cell lines or drug perturbation measurements. These data may be determined by proteomics, transcriptomics and/or genomics; and from the top right side, from a pathway signaling network 306. This may represent a disease model from known public databases, derived from measurements, influenced by known models from literature, or other sources for the model.

That dynamic simulation 302 (e.g., MCMC [Markov-Chain-Monte-Carlo] simulation) may be based on SDEs (stochastic differential equations), ODEs (ordinary differential equations), a Boolean model, and/or PDEs (partial differential equations).

In a next step of the method, the interaction-aware clustering 308 is performed. As mentioned above, a metric based on graph properties may use a Laplacian matrix, a deformed Laplacian matrix, a symmetric, normalized Laplacian matrix, random walk Laplacian matrix and/or a Vicus matrix.

Last but not least, and seen as an extension to the core inventive concept proposed here, a determination of relevant sub-groups of the clustering step may be performed, 310.

In the more basic Boolean model, a classification of steady states is required in order to enable a systematic analysis. As examples, the methods k-means clustering, DBSCAN and hierarchical clustering have been discussed as examples already. Most of the clustering methods require a distance metric which is used to compute the similarity between two states. States close to each other, i.e., having a short distance between their profiles, lie in the same cluster. For computing the distance, distance metrics like the Manhattan distance or the Euclidean distance may be used. These metrics do not work well for discrete data and also completely ignore the underlying molecular interactions. This may result in patients with a short distance between them in one cluster even though the patients' underlying molecular interactions (network graph) are very different.

However, the above phenomenon is more compelling and obvious when considering discrete states. If the state $s_1$ has a valuation "1011", the states $s_1$ has the following values of genes: $g_0=1$, $g_1=1$, $g_2=0$, and $g_3=1$. If two additional states $s_2=1001$ and $s_3=1001$ are considered, the distance of s1 to $s_2$ and $s_3$ is the same even though they differ in values of different genes. This solution to this problem is to consider the underlying graph of molecular interaction while computing the metric, i.e., interaction-aware metric.

For completeness reasons, FIG. 4 shows a block diagram of an embodiment of the disease analysis system 400 for an efficient analysis of genetic disease progression. The system 400 comprises a receiving unit 402 adapted for receiving data about a set of molecular statuses, a prediction module 404 adapted for a dynamic prediction model of molecular interactions over time, a determination unit 406 adapted for determining the molecular statuses of the set over time using the dynamic prediction model, and a clustering module 408 adapted for clustering the determined molecular statuses by applying an interaction-aware metric to analyze genetic disease progression.

Embodiments of the invention may be implemented together with virtually any type of computer, regardless of the platform being suitable for storing and/or executing program code. FIG. 5 shows, as an example, a computing system 500 suitable for executing program code related to the proposed method.

The computing system 500 is only one example of a suitable computer system, and is not intended to suggest any limitation as to the scope of use or functionality of embodiments of the invention described herein, regardless, whether the computer system 500 is capable of being implemented and/or performing any of the functionality set forth hereinabove. In the computer system 500, there are components, which are operational with numerous other general purpose or special purpose computing system environments or configurations. Examples of well-known computing systems, environments, and/or configurations that may be suitable for use with computer system/server 500 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like. Computer system/server 500 may be described in the general context of computer system-executable instructions, such as program modules, being executed by a computer system 500. Generally, program modules may include routines, programs, objects, components, logic, data structures, and so on that perform particular tasks or implement particular abstract data types. Computer system/server 500 may be practiced in distributed cloud computing environments where tasks are performed by remote processing devices that are linked through a communications network. In a distributed cloud computing environment, program modules may be located in both, local and remote computer system storage media, including memory storage devices.

As shown in the figure, computer system/server 500 is shown in the form of a general-purpose computing device. The components of computer system/server 500 may include, but are not limited to, one or more processors or processing units 502, a system memory 504, and a bus 506 that couple various system components including system memory 504 to the processor 502. Bus 506 represents one or more of any of several types of bus structures, including a memory bus or memory controller, a peripheral bus, an accelerated graphics port, and a processor or local bus using any of a variety of bus architectures. By way of example, and not limiting, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus. Computer system/server 500 typically includes a variety of computer system readable media. Such media may be any available media that is accessible by computer system/server 500, and it includes both, volatile and non-volatile media, removable and non-removable media.

The system memory 504 may include computer system readable media in the form of volatile memory, such as random access memory (RAM) 508 and/or cache memory 510. Computer system/server 500 may further include other removable/non-removable, volatile/non-volatile computer system storage media. By way of example only, a storage system 512 may be provided for reading from and writing to a non-removable, non-volatile magnetic media (not shown and typically called a 'hard drive'). Although not shown, a magnetic disk drive for reading from and writing to a removable, non-volatile magnetic disk (e.g., a 'floppy disk'), and an optical disk drive for reading from or writing to a removable, non-volatile optical disk such as a CD-ROM, DVD-ROM or other optical media may be provided. In such instances, each can be connected to bus 506 by one or more data media interfaces. As will be further depicted and described below, memory 504 may include at least one program product having a set (e.g., at least one) of program modules that are configured to carry out the functions of embodiments of the invention.

The program/utility, having a set (at least one) of program modules 516, may be stored in memory 504 by way of example, and not limiting, as well as an operating system, one or more application programs, other program modules, and program data. Each of the operating systems, one or more application programs, other program modules, and program data or some combination thereof, may include an implementation of a networking environment. Program modules 516 generally carry out the functions and/or methodologies of embodiments of the invention, as described herein.

The computer system/server 500 may also communicate with one or more external devices 518 such as a keyboard, a pointing device, a display 520, etc.; one or more devices that enable a user to interact with computer system/server 500; and/or any devices (e.g., network card, modem, etc.) that enable computer system/server 500 to communicate with one or more other computing devices. Such communication can occur via Input/Output (I/O) interfaces 514. Still yet, computer system/server 500 may communicate with one or more networks such as a local area network (LAN), a general wide area network (WAN), and/or a public network (e.g., the Internet) via network adapter 522. As depicted, network adapter 522 may communicate with the other components of the computer system/server 500 via bus 506. It should be understood that, although not shown, other hardware and/or software components could be used in conjunction with computer system/server 500. Examples, include, but are not limited to: microcode, device drivers, redundant processing units, external disk drive arrays, RAID systems, tape drives, and data archival storage systems, etc.

Additionally, the disease analysis system 400 for an efficient analysis of genetic disease progression may be attached to the bus system 506.

The descriptions of the various embodiments of the present invention have been presented for purposes of illustration, but are not intended to be exhaustive or limited to the embodiments disclosed. Many modifications and variations will be apparent to those of ordinary skills in the art without departing from the scope and spirit of the described embodiments. The terminology used herein was chosen to best explain the principles of the embodiments, the practical application or technical improvement over technologies found in the marketplace, or to enable others of ordinary skills in the art to understand the embodiments disclosed herein.

The present invention may be embodied as a system, a method, and/or a computer program product. The computer program product may include a computer readable storage medium (or media) having computer readable program instructions thereon for causing a processor to carry out aspects of the present invention.

The medium may be an electronic, magnetic, optical, electromagnetic, infrared or a semi-conductor system for a propagation medium. Examples of a computer-readable medium may include a semi-conductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W), DVD and Blu-Ray-Disk.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disk read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object-oriented programming language such as Smalltalk, C++ or the like, and conventional procedural programming languages, such as the "C" programming language or similar programming languages. The computer readable program instructions may execute entirely on the user's computer, partly on the user's computer as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatuses, or another device to cause a series of operational steps to be performed on the computer, other programmable apparatus or other device to produce a computer implemented process, such that the instructions which execute on the computer, other programmable apparatuses, or another device implement the functions/acts specified in the flowchart and/or block diagram block or blocks.

The flowcharts and/or block diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or act or carry out combinations of special purpose hardware and computer instructions.

The terminology used herein is for the purpose of describing particular embodiments only and is not intended to limit the invention. As used herein, the singular forms "a", "an" and "the" are intended to include the plural forms as well, unless the context clearly indicates otherwise. It will further be understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or steps plus function elements in the claims below are intended to include any structure, material, or act for performing the function in combination with other claimed elements, as specifically claimed. The description of the present invention has been presented for purposes of illustration and description, but is not intended to be exhaustive or limited to the invention in the form disclosed. Many modifications and variations will be apparent to those of ordinary skills in the art without departing from the scope and spirit of the invention. The embodiments are chosen and described in order to best explain the principles of the invention and the practical application, and to enable others of ordinary skills in the art to understand the invention for various embodiments with various modifications, as are suited to the particular use contemplated.

What is claimed is:

1. A computer-implemented method for an analysis of genetic disease progression, said method comprising:
    receiving data of a set of molecular statuses;
    providing a dynamic prediction model of molecular interactions over time;
    determining said molecular statuses of said set over time using said dynamic prediction model; and
    clustering said determined molecular statuses by applying an interaction-aware metric for said analysis of said genetic disease progression, the interaction-aware metric including a framework of determining distances considering a network topology of interacting genes, wherein the interaction-aware metric that determines the distances considers multidimensional molecular interaction representing at least an influence of a concentration of a gene on another gene, wherein the clustering considers underlying molecular interactions in addition to distances between the molecular statuses.

2. The method according to claim 1, wherein said dynamic prediction model is selected out of said group comprising a Boolean model, a set of ordinary differential equations, a set of stochastic differential equations, a set of partial differential equations.

3. The method according to claim 1, wherein said set of molecular statuses is represented by measurement values of a patient, a cell line or drug perturbations.

4. The method according to claim 1, wherein said dynamic prediction model and related parameters are downloadable from a remote database.

5. The method according to claim 1, wherein said interaction-aware metric is at least in parts based on a Laplacian matrix, a deformed Laplacian matrix, a symmetric Laplacian matrix, a random walk Laplacian matrix and/or a Vicus matrix.

6. The method according to claim 1, wherein said analysis of said genetic disease progression comprises
    determining a personalized therapy.

7. The method according to claim 1, also comprising
    determining a disease sub-type based on said clustering.

8. The method according to claim 1, wherein said clustering is based on at least one algorithm selected out of said group k-means, DBSCAN, and hierarchical clustering.

9. The method according to claim 1, wherein as distance measure during said clustering a Manhattan distance or an Euclidean distance is determined.

10. The method according to claim 9, wherein said distance determination is also a function of said interaction-aware metric.

11. A disease analysis system for an analysis of genetic disease progression, said system comprising
    a receiving unit adapted for receiving data about a set of molecular statuses;
    a prediction module adapted for a dynamic prediction model of molecular interactions over time;
    a determination unit adapted for determining said molecular statuses of said set over time using said dynamic prediction model; and
    a clustering module adapted for clustering said determined molecular statuses by applying an interaction-aware metric to analyze genetic disease progression, the interaction-aware metric including a framework of determining distances considering a network topology of interacting genes, wherein the interaction-aware metric that determines the distances considers multidimensional molecular interaction representing at least an influence of a concentration of a gene on another gene, wherein the clustering considers underlying molecular interactions in addition to distances between the molecular statuses.

12. The system according to claim 11, wherein said dynamic prediction model is selected out of said group comprising a Boolean model, a set of ordinary differential equations, a set of stochastic differential equations, a set of partial differential equations.

13. The system according to claim 11, wherein said data of said set of molecular statuses is represented by measurement values of a patient, a cell line or drug perturbations.

14. The system according to claim 11, also comprising
    a download module adapted for downloading said dynamic prediction model and related parameters from a remote database.

15. The system according to claim 11, wherein said interaction-aware metric is at least in parts based on a Laplacian matrix, a deformed Laplacian matrix, a symmetric Laplacian matrix, a random walk Laplacian matrix and/or a Vicus matrix.

16. The system according to claim 11, also comprising
    personalization determination module adapted for a determination of a personalized therapy as part of said analysis of said genetic disease progression.

17. The system according to claim 11, wherein said clustering module unit is also adapted for
    determining a disease sub-type.

18. The system according to claim 11, wherein said clustering module unit is adapted for performing at least one algorithm selected out of said group k-means, DBSCAN, and hierarchical clustering.

19. The system according to claim 11, wherein as distance measure during said clustering a Manhattan distance or an Euclidean distance is determined.

20. A computer program product for an efficient analysis of genetic disease progression, said computer program product comprising a non-transitory computer readable storage medium having program instructions embodied therewith, said program instructions being executable by a computer to cause said computer to:
- receive data about a set of molecular statuses;
- provide a dynamic prediction model of molecular interactions over time;
- determine said molecular statuses of said set over time using said dynamic prediction model; and
- cluster said determined molecular statuses by applying an interaction-aware metric to analyze genetic disease progression, the interaction-aware metric including a framework of determining distances considering a network topology of interacting genes, wherein the interaction-aware metric that determines the distances considers multidimensional molecular interaction representing at least an influence of a concentration of a gene on another gene, wherein clustering considers underlying molecular interactions in addition to distances between the molecular statuses.

* * * * *